United States Patent [19]

Chang

[11] Patent Number: 5,290,704
[45] Date of Patent: Mar. 1, 1994

[54] METHOD OF DETECTING ORGANIC SOLVENT VAPORS

[75] Inventor: On-Kok Chang, San Jose, Calif.

[73] Assignee: Valence Technology, Inc., San Jose, Calif.

[21] Appl. No.: 34,933

[22] Filed: Mar. 19, 1993

[51] Int. Cl.$^5$ ..................... G01N 33/00; G01N 21/77
[52] U.S. Cl. ..................... 436/128; 436/167; 436/169; 436/171; 422/86
[58] Field of Search ................. 422/86; 436/167, 169, 436/127, 131, 132, 139, 128, 130, 171; 503/200, 203, 218

[56] References Cited

U.S. PATENT DOCUMENTS

| | | | |
|---|---|---|---|
| 4,151,748 | 5/1979 | Baum | 73/356 |
| 4,246,518 | 1/1981 | Baum | 428/411 |
| 4,470,057 | 9/1984 | Glanz | 346/209 |
| 4,786,629 | 11/1988 | Kawakami et al. | 503/200 |
| 4,826,772 | 5/1989 | Meathrel | 436/93 |
| 4,855,282 | 8/1989 | Satomura et al. | 503/218 |
| 5,151,403 | 9/1992 | Suzuki et al. | 503/200 |

*Primary Examiner*—James C. Housel
*Assistant Examiner*—N. Bhat
*Attorney, Agent, or Firm*—S. Russell La Paglia

[57] ABSTRACT

A photometric detector is used to detect the presence of organic solvent vapors in the air. The detector need only be exposed to the air in the area to be tested. The optical density, i.e. darkness of the color of the detector determines the cumulative amount of solvent vapor exposure and the rate at which the dark color develops determines the concentration of solvent vapors in the air. This method can be used to quickly and easily test for harmful levels of toxic organic solvent vapors in the workplace or elsewhere.

9 Claims, No Drawings

METHOD OF DETECTING ORGANIC SOLVENT VAPORS

FIELD OF THE INVENTION

The present invention relates to a method for easily and continuously detecting organic solvent vapors in the air. More specifically, the present invention relates to a method for detecting organic solvent vapors in the air by exposing a suitable chromogenic material to the air to be tested and analyzing it for discoloration caused by the organic solvent vapors.

BACKGROUND OF THE INVENTION

Organic vapors in the atmosphere pose an large environmental concern. For this reason there have been developed several methods for monitoring organic vapors. For example, photo-ionization detectors are relatively sensitive instruments. However, they are quite expensive and not very suitable for continuous monitoring. Analyzers which use Drägger tubes provide good selectivity toward differing organic vapors. However, in order to detect cumulative exposure to a number of different types of organic vapors, each type of organic compound must be analyzed with a different tube and then the results must be combined. These types of analyzers are also not suitable for continuous monitoring. Passive monitor badges such as those produced by SKC West, Inc., have been used to detect organic vapors. However, these badges are really only collection devices. Consequently, a badge has to be analyzed in a laboratory to give information about organic vapor content. Thus, there exists considerable need for a quick, reliable and inexpensive method to detect and/or monitor the presence of organic vapors in the air. It would also be highly desirable if this method could provide for continuous monitoring of a given environment. It would be advantageous if the vapor content of the air could be continuously monitored in a quantitative manner.

Thermally-responsive record materials are well known in the art and are described in a number of patents, for example, U.S. Pat. Nos., 3,539,375; 3,674,535; 3,746,675; 4,151,748; 4,181,771; 4,246,318 and 4,470,057 which are incorporated herein by reference. In these systems, basic chromogenic material and acidic developer material are contained in a coating on a substrate which, when heated to a suitable temperature, melts or softens to permit the materials to react, thereby producing a colored mark. A method for as quickly and easily detecting and/or monitoring the presence of organic solvent vapors in the air would be desirable.

A method for continuously determining the cumulative amount of exposure to organic solvent vapors in a selected area such as a workplace environment would be desirable.

An accurate method of determining the concentration of organic solvent vapors in the air in a selected environment would also be desirable.

SUMMARY OF THE INVENTION

Accordingly, the present invention provides a photometric organic solvent vapor detector made of a substrate, a binder means which is substantially soluble to the solvent vapor, an electron donating chromogenic composition dispersed on the substrate in connection with the binder means, and an electron accepting composition, which forms a color with the chromogenic composition, dispersed on the substrate in connection with the binder means. The present invention includes a method of making the described detector, including the step of selecting a binder means which is substantially soluble to the solvent to be detected. Preferably, the binder means is selectively substantially soluble to the solvent, or the class of compounds to which the solvent belongs. The present invention also includes the method of detecting organic solvent vapor by exposing the described detector to solvent vapors, and photometrically measuring the optical density of the detector. In a preferred embodiment the detector means includes a photometer. In practice, when the environment is suspected of containing organic solvent vapors, the detector is continuously monitored visually, or preferably by a photometer. The photometer continuously reads the optical density of the detector which is interposed in the photometer's light beam between the light source and the light sensitive cell. If solvent vapor is present in detectable amount the optical density of the detector will continuously increase. The rate of increase of the optical density is directly proportional to the solvent vapor concentration in the air. The optical density at elapsed time, T, measures the total exposure to solvent vapor during that time interval. If qualitative indications of the presence of solvent vapors in the environment will suffice, the detector may be posted, or worn as a small card or badge, for visual inspection.

The detectors and methods of the present invention are effective in detecting a vast array of organic solvents and/or organic solvent-containing materials. It is preferred, however, that the organic solvent is a polar solvent, i.e., one having a dielectric constant of greater than about 8, and preferably greater than about 12, and more preferably greater than about 16. The present method is also useful in detecting substantially all heteroatom-containing solvents.

Several examples of preferred polar solvents and heteroatom-containing solvents include the following: alcohols such as methanol, ethanol, propanol, isopropanol, butanol, etc.; small molecule ketones such as those having less than about 6 carbon atoms; small molecule esters such as those having less than about 8 carbon atoms; acetone; dimethylsulfoxide; dioxolanes; sulfolanes; butyrolactones; tetrahydrofurans; ethers such as glyme, diglyme, triglyme, tetraglyme, octaglyme, etc.; and alkyl carbonates such as propylene carbonate and the like. The invention is also applicable to a number of additional solvents not specifically enumerated above. The method of the invention is also capable of detecting a wide range of organic solvent-containing materials. One such example is electrolytes such as those used in manufacturing electrolytic cells, e.g., solid batteries.

In general, the binder means is selected to be soluble to an organic solvent vapor whose presence it is desired to detect. However, the binder means will normally be soluble to a whole class of organic solvent vapors.

The binder means performs several functions. Primarily, the binder means serves to improve the adhesion of the chromogenic composition and the developer (electron accepting composition) to the substrate. The binder means can also serve to protect the dispersed compositions from brushing and handling forces. So-called thermal papers also contain a waxy substance in the binder means which is selected to melt at a prescribed temperature. Binders also encompass the microencapsulation of the color-forming compositions of this invention. Most importantly, in the practice of this invention, the binder means serves as a means of keeping the color-forming compositions apart until the binder-means is solubilized by the organic solvent vapors. The binder means may consist of 3 or more separate and distinct compositions or materials to perform these and other functions disclosed in the art. But taken in its entirety, the functions and the compositions of materials chosen to perform those functions are herein referred to as the binder-means. Binder means are disclosed in U.S. Pat. Nos. 4,855,282; 5,151,403; 4,470,057; 4,786,629; 4,586,061; 4,794,102; 4,535,347; 4,688,059; 4,403,791; 4,601,588 the disclosure of each is herein incorporated by reference as if fully stated in ipsis verbis. Binder means for the purposes of this invention encompasses all of the foregoing, and such portions of these compositions and materials as are necessary to permit photometric organic vapor solvent detection according to the present method.

Suitable binders which can be used include water-soluble high molecular weight substances and water-insoluble binders, which are used alone or in combination. Suitable water-soluble high molecular weight substances include methylcellulose, carboxymethylcellulose, hydroxyethyl cellulose, starches, gelatin, gum arabic, casein, hydrolysis products of copolymers of styrene and maleic anhydride, hydrolysis products of copolymers of ethylene and maleic anhydride, hydrolysis products of copolymers of isobutylene and maleic anhydride, polyvinyl alcohol, carboxy modified polyvinyl alcohol and polyacrylamide. Suitable water insoluble binders include generally synthetic rubber latexes and synthetic resin emulsions, such as styrene and butadiene rubber latex, acrylonitrile and butadiene rubber latex, methyl acrylate and butadiene rubber latex or a vinyl acetate emulsion.

The additive amount of binders is from 3 to 100%, preferably from 5 to 50% based on the weight of the pigments. Wax, fade preventing agents and surface active agents can be added if desired.

Eligible chromogenic compounds, such as the phthalide, leucauramine and fluoran compounds, for use in the color-forming system are well known color-forming compounds. Examples of suitable color-forming compounds include Crystal Violet Lactone (3,3-bis(4-dimethylaminophenyl)-6-dimethylaminophthalide, U.S. Pat. No. Re. 23,024); phenyl-, indol-, pyrrol-, and carbazol-substituted phthalides (for example, in U.S. Pat. Nos. 3,491,111; 3,491,112; 3,491,116; 3,509,174); nitro-, amino-, amido-, sulfon amido-, aminobenzylidene-, halo-, anilino-substituted fluorans (for example, in U.S. Pat. Nos. 3,624,107; 3,627,787; 3,641,011; 3,642,828; 3,681,390); spirodipyrans (U.S. Pat. No. 3,971,808); and pyridine and pyrazine compounds (for example, in U.S. Pat. Nos. 3,775,424 and 3,853,869). Other specifically eligible chromogenic compounds, not limiting the invention in any way, are: 3-diethylamino-6-methyl-7-anilino-fluoran (U.S. Pat. Nos. 3,681,390); 7-(1-ethyl-2-methylindol-3-yl)-7-(4-diethylamino-2-ethoxyphenyl)-5,7-dihydrofuro[3,4-b]pyridin-5-one (U.S. Pat. No. 4,246,318); 3-diethylamino-7-(2-chloroanilino)fluoran (U.S. Pat. No. 3,920,510); 3-(N-methylcyclohexylamino)-6-methyl-7-anilinofluoran (U.S. Pat. No. 3,959,571); 7-(1-octyl-2-methylindol-3-yl)-7-(4-diethylamino-2-ethoxyphenyl)-5,7-dihydrofuro[3,4-b]-pyridin-5-one; 3-diethylamino-7,8-benzofluoran; 3,3-bis(1-ethyl-2-methylindol-3-yl)phthalide; 3-diethylamino-7-anilinofluoran; 3-diethylamino-7-benzylaminofluoran; and 3'-phenyl-7-dibenzylamino-2,2'-spiro-di-[2H-1-benzopyran].

The electron-accepting compound which forms a color on contact with the electron-donating colorless dye polymer can be any of the conventional developer compounds known to be capable of color formation, as described in U.S. Pat. Nos., 3,491,111, 3,491,112, 3,491,116, 3,509,174, 3,624,107, 3,627,787, 3,641,011, 3,462,828, 3,681,390, 3,920,510, 3,959,571, 3,971,808, 3,775,424, 3,853,869, 4,246,318, 4,480,052, and 4,436,920, British Pat. Nos. 2,140,449, 1,018,793, 2,166,882, 2,165,953, 2,162,650, 2,156,535, and 2,154,014, Japanese Patent Publication No. 23922/85, and Japanese Patent Application (OPI) Nos. 179836/82, 123556/85, and 123557/85. Examples of the electron-accepting compound include phenol derivatives, salicylic acid derivatives, metal salts of aromatic carboxylic acids, and acid clay.

Specific examples of the electron-accepting compound include organic developers such as 4-tertiary butyl phenol; 4-phenylphenol; 2,2-bis(4-hydroxyphenyl)propane (i.e., bisphenol A); 4,4'-isopropylidene-bis(2-methylphenol); 1,1-bis(3-chloro-4-hydroxyphenyl)cyclohexane; 1,1-bis(3-chloro-4-hydroxyphenyl)-2-ethyl butane; 4,4'-secondary isooctylidene diphenol; 4-tert-octyl phenol; 4,4'-sec-butylidene diphenol; 4-chlorophenylphenol; 4,4'-isopentylidene diphenol; 4,4'-methylcyclohexylidene diphenol; 4,4'-dihydroxydiphenyl sulfide; 1,4-bis-4'-hydroxycumyl benzene; 1,3-bis-4'-hydroxycumyl benzene; 4,4'-thiobis(6-tert-butyl-3-methyl phenol); 4,4'-dihydroxydiphenyl sulfone; hydroquinone monobenzyl ether; 4-hydroxybenzophenone; 2,4-dihydroxybenzophenone; polyvinyl benzyloxycarbonyl phenol; 2,2',4,4'tetrahydroxybenzophenone; dimethyl 4-hydroxylphthalate; methyl 4-hydroxybenzoate; 2,4,4'-trihydroxydiphenyl sulfone; 1,5-bis-p-hydroxyphenyl pentane; 4-hydroxybenzoic α-phenylbenzyl ester; phenylpropyl 4-hydroxybenzoate; phenethyl 4-hydroxybenzoate; p-chlorobenzyl 4-hydroxybenzoate; p-methoxybenzyl 4-hydroxybenzoate; 4-hydroxybenzoic benzyl ester; 4-hydroxy-2',4'-dimethyldiphenyl sulfone; β-phenethylorsellinate; cinnamyl orsellinate; orsellinic-o-chlorophenoxyethyl ester; o-ethylphenoxyethyl orsellinate; o-phenylphenoxyethyl orsellinate; 2,4-dihydroxybenzoic-β-3'-t-butyl-4'-hydroxyphenoxyethyl ester; stearyl gallate; 4-N-benzylsulfamoyl phenol; 2,4-dihydroxybenzoic-β-phenoxyethyl ester; 2,4-dihydroxy-6-methylbenzoic benzyl ester; allyl bis-4-hydroxyphenyl acetate; ditolyl thiourea; 4,4'-diacetyldiphenyl thiourea; 3-phenyl salicylic acid; orsellinic-β-o-methoxyphenoxyethyl ether; orsellinic trioxyethyl ester: orsellinic-β-p-methoxyphenoxypropyl ester; β-resorcylic phenoxyethyl ether; β-resorcylic-δ-p-methoxyphenoxybutyl ester; phenylphenol-formaldehyde resin; and p-butylphenolacetylene resin; polyvalent metal salts formed of these organic developers with zinc, magnesium, aluminum, and calcium; and inorganic developers such as acid clay, activated clay, attapulgite, aluminum silicate, magnesium silicate, zinc rhodanate and complexes thereof, and zinc chloride.

Two or more of the developers enumerated above may be used in combination. Any of these developers may be used in combination with one or more members selected from at least the following inorganic developers such as iron stearate, cobalt naphthenate, nickel peroxide, and ammonium sulfate; aliphatic carboxylic acids such as oxalic acid, maleic acid, tartaric acid, citric acid, succinic acid, and stearic acid; and other organic acids such as benzoic acid, para-tertiary butylbenzoic acid, phthalic acid, or gallic acid.

Examples of eligible acidic developer material include the compounds listed in U.S. Pat. No. 3,539,375 as phenolic reactive material, particularly the monophenols and diphenols. Eligible acidic developer material also includes, without being considered as limiting, the following compounds which may be used individually or in mixtures: 4,4'-isopropylidinediphenol (Bisphenol A); p-hydroxybenzaldehyde; p-ydroxybenzophenone; p-hydroxypropiophenone; 2,4-dihydroxybenzophenone; 1,1-is(4-hydroxy-3-methylphenyl)-cyclohexane; 1,1-bis(4-hydroxyphenyl)cyclohexane; salicylanilide; 4-hydroxy-2-methylacetophenone; 2-acetylbenzoic acid; m-hydroxyacetanilide; p-hydroxyacetanilide; 2,4-dihydroxyacetophenone; 4-hydroxy-4'-methylbenzophenone; 4,4'-dihydroxybenzophenone; 2,2-bis-(4-hydroxyphenyl)-4-methylpentane; benzyl 4-hydroxyphenyl ketone; 2,2-bis(4-hydroxyphenyl)-5-methylhexane; ethyl-4,4-bis(4-hydroxyphenyl)-pentanoate; n-propyl-4,4-bis(4-hydroxyphenyl)pentanoate; isopropyl-4,4-bis(4-hydroxyphenyl)pentanoate; methyl-4,4-bis(4-hydroxyphenyl)pentanoate; 3,3-bis(4-hydroxyphenyl)-pentane; 4,4-bis(4-hydroxyphenyl)-heptane; 2,2-bis(4-hydroxyphenyl)-1-phenylpropane; 2,2-bis(4-hydroxyphenyl)butane; 2,2'-methylene-bis(4-ethyl-6-tertiarybutyl phenol); 4-hydroxycoumarin; 7-hydroxy-4-methylcoumarin; 2,2'-methylene-bis(4-octyl phenol); 4,4'-sulfonyldiphenol; 4,4'-thiobis(6-tertiarybutyl-m-cresol); methyl-p-hydroxybenzoate; n-propyl-p-hydroxybenzoate; benzyl-p-hydroxybenzoate. Preferred among these are the phenolic developer compounds. More preferred among the phenol compounds are 4,4'-isopropylidinediphenol; ethyl-4,4-bis(4-hydroxyphenyl)pentanoate; n-propyl-4,4-bis(4-hydroxyphenyl)pentanoate; isopropyl-4,4-bis(4-hydroxyphenyl)pentanoate; methyl-4,4-bis(4-hydroxyphenyl)pentanoate; 2,2-bis(4-hydroxyphenyl)-4-methylpentane; p-hydroxybenzophenone; 2,4-dihydroxybenzophenone; and 1,1-bis(4-hydroxyphenyl)cyclohexane. Acid compounds of other kinds and types are eligible. Examples of such other compounds are phenolic resins which are the product of reaction between, for example, formaldehyde and a phenol such as an alkylphenol, e.g., p-octylphenol, or other phenols such as p-phenylphenol, and the like; and acid mineral materials including colloidal silica, kaolin, bentonite, attapulgite, hallosyte, and the like.

The organic solvent vapor detector also includes a support or substrate as part of the overall composite. The support or substrate material is typically in sheet form. For purposes of this invention, sheets also mean webs, ribbons, tapes, belts, films, cards and the like. The substrate or support material can be opaque, transparent or translucent and could, itself, be colored or not. For use with a photometer it is preferred that the substrate, and the entire vapor detector, be substantially transparent or translucent to the metering light of the photometer. The substrate can be fibrous including, for example, paper and filamentous synthetic materials. It can be a film including, for example, cellophane and synthetic polymeric sheets cast, extruded, or otherwise formed.

The thickness of the substrate material is generally on the order of about 50–100 μm. The thickness may, however, be varied as desired without substantially affecting the method of the present invention.

The components of the color-forming system are in a contiguous relationship, substantially homogeneously distributed throughout the coated layer material deposited on the substrate. In manufacturing the preferred detector, a coating composition is prepared which includes a fine dispersion of the components of the color-forming system, polymeric binder material, surface active agents and other additives in an aqueous coating medium. The composition can additionally contain inert pigments, such as clay, talc, aluminum hydroxide, calcined kaolin clay and calcium carbonate; synthetic pigments, such as urea-formaldehyde resin pigments; natural waxes such as Carnuba wax; synthetic waxes; lubricants such as zinc stearate; wetting agents and defoamers.

The color-forming system components are substantially insoluble in the dispersion vehicle (preferably water) and are ground to an individual average particle size of between about 1 micron to about 10 microns, preferably about 3 microns. The preferred polymeric binder means is substantially vehicle soluble although latexes are also eligible in some instances. Preferred water soluble binders include polyvinyl alcohol, hydroxy ethylcellulose, methylcellulose, methyl-hydroxypropylcellulose, starch, modified starches, gelatin and the like. Eligible latex materials include polyacrylates, polyvinylacetates, polystyrene, and the like. The polymeric binder is also used to protect the coated materials from brushing and handling forces occasioned by storage and use. Binder should be present in an amount to afford such protection and in an amount less than will interfere with achieving reactive contact between color-forming reactive materials.

The method of the invention provides a quick, easy and inexpensive method of detecting and/or monitoring, without separate analysis, contamination of an area by an organic solvent vapor. Additionally, the present method may also be used to determine the amount of cumulative exposure to organic solvent vapors as well as to determine the concentration of organic solvent vapors in a given area.

In particular, the present invention is able to determine the amount of cumulative exposure to organic solvent vapors by analyzing the optical density of the detector, i.e., the greater the optical density, the greater the cumulative exposure to organic solvent vapors. In this same way the present invention is able to determine the concentration of organic solvent vapors in an area by analyzing the rate at which the detector develops a dark color, i.e., the faster the color develops, the higher the concentration of organic solvent vapor.

In the practice of the method of this invention the organic solvent vapor detector is exposed to the airborne solvent vapors, and the optical density of the detector is photometrically measure to quantitively determine the rate of solvent contamination of the air, and the total amount of solvent that has contaminated the air over an elapsed time. If the binder means has been selectively chosen, the class of chemicals to which the solvent belongs can also be determined. The photometric devices used in the practice of the present invention to measure optical density are well known in the art. Such photometers may either be sensitive in the visible portion of the spectrum or in the ultra violet, or in both regions.

The selection of a binder means for substantial solubility to a particular organic solvent vapor, or to a class of organic solvent vapors, is well within the skill of those with access to tables of solubilities. The selection of such binder-means is the determining step in the method of making a photometric organic solvent vapor detector.

In order to further illustrate the present invention and the advantages thereof, the following specific examples are given, it being understood that the same are intended as illustrative and in no way limitative.

EXAMPLE

The following example was conducted to determine the ability of thermal paper to detect and/or monitor organic solvent vapors.

A few cc of an organic solvent was added to a 20 ml vial. The vial was capped and shaken to help the solvent evaporate. The cap was then removed to expose the solvent to the air.

A small piece of thermal paper, commercially available from Hewlett Packard (Part No. 92700650), was cut into a strip, folded into the shape of a "V" and placed in the opening of the open vial, heat sensitive side down as depicted below:

A dark color developed on the thermal paper exposed to acetone. A lighter color developed on the thermal paper exposed to propylene carbonate. Almost no color developed on the thermal paper exposed to isopropyl alcohol. Also, the color of thermal paper was generally darker the longer it was exposed to the open vial of solvent.

While the invention has been described in terms of various preferred embodiments, the skilled artisan will appreciate the various modifications, substitutions, omissions, and changes may be made without departing from the spirit thereof.

What is claimed is:

1. A method of detecting organic solvent vapor comprises the steps of:
   (a) exposing a solvent vapor detector to solvent vapor; and
   (b) photometrically measuring the optical density of said detector; wherein said detector comprises:
   a substrate;
   a binder means which is substantially soluble to said solvent vapor;
   an electron donating chromogenic composition dispersed on said substrate in connection with said binder means; and
   an electron accepting composition, which forms a color with said chromogenic composition, dispersed on said substrate in connection with said binder means.

2. The method of claim 1, wherein said organic solvent comprises at least one polar solvent having a dieletric constant greater than about 8.

3. The method of claim 2, wherein said polar solvent has a dieletric constant greater than about 12.

4. The method of claim 3, wherein said polar solvent has a dieletric constant greater than about 16.

5. The method of claim 2, wherein said polar solvent comprises at least one alcohol, glycol, polyol, aldehyde, carbonate, acetone, ester, ether, ketone, dimethylsulfoxide, glyme, dioxalane, sulfulane, gamma-butyrolactone and tetrahydrofuran.

6. The method of claim 5, wherein said alcohol contains less than about 8 carbon atoms.

7. The method of claim 5, wherein said ketone contains less than about 6 carbon atoms.

8. The method of claim 5, wherein said esters contain less than about 8 carbon atoms.

9. The method of claim 1, wherein said detector comprises a photometer sensitive to visible or ultraviolet light.

* * * * *